(12) United States Patent
Genova et al.

(10) Patent No.: US 6,418,925 B1
(45) Date of Patent: Jul. 16, 2002

(54) LOW SPRAY FORCE, LOW RETENTION ATOMIZATION SYSTEM

(75) Inventors: Perry A. Genova, Chapel Hill; Robert C. Williams, III, Raleigh; Warren Jewett, Cary, all of NC (US)

(73) Assignee: IEP Pharmaceutical Devices Inc., Raleigh, NC (US)

( * ) Notice: Subject to any disclaimer, the term of this patent is extended or adjusted under 35 U.S.C. 154(b) by 0 days.

(21) Appl. No.: 09/570,115

(22) Filed: May 12, 2000

Related U.S. Application Data (60) Provisional application No. 60/135,056, filed on May 20, 1999.

(51) Int. Cl.$^7$ .............................................. A61M 11/00
(52) U.S. Cl. ............................ 128/200.14; 128/200.23; 239/463
(58) Field of Search ................. 128/200.11, 200.12, 128/200.14, 200.16–200.18, 200.21–200.24, 203.12, 203.15, 203.21; 604/58; 239/463, 466, 474, 491

(56) References Cited

U.S. PATENT DOCUMENTS

| | | | |
|---|---|---|---|
| 2,974,880 A | | 3/1961 | Stewart et al. |
| 4,241,877 A | | 12/1980 | Hughes |
| 4,260,110 A | * | 4/1981 | Werding .................. 239/404 |
| 4,702,415 A | * | 10/1987 | Hughes ........................ 239/8 |
| 4,852,561 A | | 8/1989 | Sperry |
| 4,926,852 A | | 5/1990 | Zoltan et al. |
| 4,953,545 A | | 9/1990 | McCarty |
| 4,972,830 A | * | 11/1990 | Wong et al. ........... 128/200.23 |
| 5,040,527 A | | 8/1991 | Larson et al. |
| 5,067,655 A | * | 11/1991 | Farago et al. ................ 239/124 |
| 5,165,391 A | | 11/1992 | Chiesi et al. |
| 5,178,138 A | | 1/1993 | Walstrom et al. |
| 5,178,331 A | * | 1/1993 | Schuerz ...................... 239/405 |
| 5,203,323 A | | 4/1993 | Tritle |
| 5,320,094 A | | 6/1994 | Laube et al. |
| 5,477,849 A | | 12/1995 | Fry |
| 5,549,102 A | | 8/1996 | Lintl et al. |
| 5,676,130 A | * | 10/1997 | Gupte et al. ........... 128/203.19 |
| 5,711,488 A | | 1/1998 | Lund |
| 5,860,416 A | * | 1/1999 | Howlett ................. 128/200.23 |
| 5,899,201 A | * | 5/1999 | Schultz et al. ......... 128/200.23 |
| 5,954,047 A | * | 9/1999 | Armer et al. ........... 128/200.23 |
| 5,983,893 A | | 11/1999 | Wetterlin |
| 6,026,808 A | | 2/2000 | Armer et al. |
| 6,062,214 A | * | 5/2000 | Howlett ................. 128/200.23 |
| 6,082,355 A | * | 7/2000 | Howlett ................. 128/200.23 |
| 6,085,742 A | * | 7/2000 | Wachter et al. ........ 128/200.23 |
| 6,095,141 A | * | 8/2000 | Armer et al. ........... 128/204.26 |

FOREIGN PATENT DOCUMENTS

| | | | | |
|---|---|---|---|---|
| DE | 21 23 519 | | 11/1972 | |
| DE | 26 25 496 | | 12/1977 | |
| FR | 1 226 549 | | 7/1960 | |
| GB | 2276101 | * | 9/1994 | ............ 128/200.23 |

* cited by examiner

*Primary Examiner*—John G. Weiss
*Assistant Examiner*—Teena Mitchell
(74) *Attorney, Agent, or Firm*—Frommer Lawrence & Haug; Ronald R. Santucci

(57) ABSTRACT

A pressure swirl atomizer for providing a low-plume aerosolized spray of liquids, solutions or other suspension which includes a swirl chamber which create shear forces which causes the spray to aerosolize.

23 Claims, 6 Drawing Sheets

LOW SPRAY FORCE, LOW RETENTION ATOMIZATION SYSTEM

This application claims the benefit of provisional application 60/135,056 filed May 20, 1999.

FIELD OF THE INVENTION

The invention relates to a nozzle to eject pressurized spray for use in a multitude of applications, including pharmaceutical applications involving inhalers.

BACKGROUND OF THE INVENTION

The present invention has a wide range of applications in which it can be used. Reference to inhalers is merely an example of one such use.

The problem associated with metered dose inhalers (MDI) of the type using a pressurized canister of aerosol is well documented in the literature and comprises maintaining small particles of medication in a low velocity mist. The prior art has attempted to solve this problem in two ways. One way modifies the MDI to include a depressurization chamber (spacer) and the other way reduces energy in the spray by a creation of vortices in the spray flow.

Laube et al, U.S. Pat. No. 5,320,094, discloses a method of delivering a protein, in particular insulin, to the lungs. The method is characterized in that an aerosolized mist of small particles is produced in an associated medicament delivery chamber, the distance from the chamber to the patient's mouth is set to slow the speed of aerosol particles entering the mouth and the flow rate through the chamber is regulated to a low rate of less than about 30 liters per minute.

Tritle, U.S. Pat. No. 5,203,323 discloses an expansion chamber used in combination with a MDI to intercept the high-velocity discharge of medicament from a pressurized inhaler. The expansion chamber has a constant volume with no moving parts or external vents for ease of cleaning, for durability, and for optimizing the mist concentration. The dimensional parameters of the chamber are optimized to produce a maximum concentration of medicament mist while neutralizing the high velocity of the inhaler discharge. The chamber is provided at one end with an inlet aperture into which the inhaler mouthpiece sealingly fits. At the chamber other end is provided an outlet aperture with a chamber mouthpiece over which a user's mouth is closed. The chamber mouthpiece aperture is sized so that substantially all of the medicament mist is uniformly withdrawn during a single short breath by a user suffering from a respiratory ailment such as asthma. One end of the chamber is a removable cap to facilitate cleaning. Also to facilitate cleaning, a brush is provided that is formed to the shape of the chamber internal dimensions. Used in combination with the chamber with the cap removed, the chamber is cleaned by the brush, typically with soap and water, and the chamber can be reused indefinitely at very nominal cost. To maintain cleanliness during nonuse, protective cover caps are provided to close the inlet and outlet apertures. Larson et al., U.S. Pat. No. 5,040,527 discloses an apparatus for dispensing a measured amount of a spray-entrapped product, typically dispensed by a metered dose inhaler device, includes an elongated passageway having a mouthpiece portion and a main chamber portion. The metered dose inhaler is mounted between the mouthpiece and main chamber portions such that upon operation its spray is directed away from the mouthpiece. A two-position valve is provided to allow a first, low-level flow to be developed through the unit, followed by a higher flow rate as the metered dose inhaler unit is operated. This increased flow, passing through the device in the direction opposite to that of the MDI spray, contacts the spray plume to cause a high level of mixing and a decrease in spray particle size which results in a draw of the spray medication into the lungs of the user.

Zoitan et al., U.S. Pat. No. 4,926,852 discloses an apparatus for use in inhaling pharmaceutical aerosols. The apparatus includes a mouthpiece and a rigid housing for receiving an aerosolized medicine. The rigid housing has one or more orifices which are spaced from the mouth piece so that flow through the housing is possible but is limited by the orifice(s) to a desired volumetric flow rate.

Hughes, U.S. Pat. No. 4,241,877 discloses a vortex generating device wherein a flow passage aligned with a flow axis is connected between a fluid inlet and a fluid outlet, and a plurality of tornado-like gas vortices are generated in the flow passage in an annular arrangement around the flow axis; the vortices also rotate about the flow axis. The combination of shock wave formation and vortex generation in a gas stream permits atomization of liquids.

Sperry, U.S. Pat. No. 4,852,561 discloses an MDI with aerosol chamber dispersion techniques to reduce such ailments as thrush and a one-way valve that allows the user to draw the drug from the aerosol chamber and exhale into the MDI without disturbing its contents or contaminating the MDI with exhaled organisms. The aerosol cartridge is located inside the aerosol chamber and is activated by a unique valve that directs the discharged contents into the aerosol chamber for aerosolization. The aerosol chamber is shaped to optimize the aerosolization process while maintaining a good shape to hold and carry about in a jacket pocket or purse.

Larson et al., U.S. Pat. No. 4,598,836 discloses a spray-entrapped product such as dispensed by an MDI device includes an elongated passageway having a mouth-piece portion and a main chamber portion. The MDI device is mounted to direct a medication spray into the main chamber. A first air inlet allows a low-level inspiratory breath to be developed through the unit prior to operation of the MDI device. When the MDI device is operated a second, air inlet is opened, allowing a higher-level breath to be developed, which causes a high level or mixing with the MDI spray for efficient draws into the lungs. The second air inlet remains open after MDI operation ceases, insuring that a complete, high flow rate breath can be made to fully sweep the medication out of the chamber.

Wong, U.S. Pat. No. 4,972,830, discloses a device for dispersing a fluid supplied from an external source having a feed supply. An inlet accepts a fluid from the feed supply for passing the fluid through an outer perimeter of the device in a downstream direction and has an axis contained in a plane. An outlet is provided downstream from the inlet for allowing the fluid to exit. A bluff body is positioned between the inlet and the outlet and has an axis contained in a plane perpendicular to the inlet axis plane. At least one passageway internal to the outer perimeter and external and extending downstream from the outlet for passing a second fluid is provided.

The prior art references described above show a variety of structures for achieving the objective of maintaining particles in a low velocity spray, including swirls, chamber shapes and vortex development. Many of the prior art devices typically retain a significant portion of the drug entering the device. This will adversely affect the uniformity of the emitted doses and decrease the absolute quantity of drug reaching the patient. This is especially characteristic of spacer devices but is also associated with the Wong device, described above. Therefore, there is still a need for a nozzle which has simple construction, small size, reliability and good atomization while generating discrete particle sizes. It is also desirable that the nozzle work well with liquids, solutions or suspensions for versatility.

While the types of vortices as aforenoted have particular advantages, they also have attendant disadvantages some of which have been mentioned.

SUMMARY OF THE INVENTION

It is therefore a principal object of the invention to overcome the shortcomings of the nozzles heretofore mentioned.

It is a further object of the invention to provide a nozzle of use in MDIs to deliver liquids, solutions and suspensions.

It is a further object of the invention to provide a nozzle which has simple construction, small size, reliability and good atomization.

It is a further object of the invention to provide a nozzle which has simple construction, small size, reliability, good atomization uniform particle size, low drug retention and more reproducible drug delivery over prior art devices.

The invention comprises a vortex nozzle to eject the pressurized spray. The nozzle comprises an inlet portion with an outlet which is tangential to the inlet of a swirl chamber through which the substance is sprayed. The design of the present invention is simpler and less costly to manufacture in comparison to the prior art nozzles. In a particular example, that will be detailed herein, the nozzle is utilized in an inhaler for aerosolized medication which may be an MDI or other type.

While the present invention has obvious utility in the delivery of aerosolized medicines to the pulmonary system of mammals and to other body parts, it should be evident that it has industrial use as well in the delivery of paints, cosmetics, hair sprays, insect repellants, lock de-icers and other anti-freezing compositions, and the like.

BRIEF DESCRIPTION OF THE DRAWINGS

Thus by the present invention its objects and advantages will be realized, the description of which should be taken in conjunction with the drawings wherein:

FIG. 1 shows a side cross sectional view of a preferred embodiment of the inventive nozzle.

FIG. 2 shows a side cross sectional view of a second preferred embodiment of the inventive nozzle.

FIG. 3 shows a side cross sectional view of a third preferred embodiment of the inventive nozzle.

FIG. 4 shows a side cross sectional view of a fourth preferred embodiment of the inventive nozzle.

FIG. 5 shows a side view of a preferred embodiment of the nozzle incorporated in an inhaler.

FIG. 6 is a top perspective view taken along arrow 6 shown in FIG. 5.

FIG. 7 is top plan view of the nozzle and mouthpiece insert of FIG. 5.

DETAILED DESCRIPTION OF THE INVENTION

Initially, in the figures, like parts are similarly numbered. FIG. 1 shows a preferred embodiment of the invention. In nozzle 10 the liquid is fed, under pressure, into a swirl chamber 12 through an inlet 14 into an inlet chamber 16 having an outlet passage 18. Outlet passage 18 is tangential to the outer circumference of swirl chamber 12. The inlet 14, particularly the outlet passage 18 in the preferred embodiment is set at an angle A, which is a 105 degree angle from the axis through exit orifice 20 but can also be perpendicular to this axis (i.e. at 90 degrees). The liquid entering swirl chamber 12 from outlet passage 18 imparts a high angular velocity creating a low pressure central region which creates an air-cored vortex. This vortex spins through swirl chamber 12 and emerges with tangential and axial components via an exit orifice 20. Here, a hollow annular spray is produced. This spray exits exit orifice 20 as a conical sheet through nozzle face 22. The air core in conjunction with the swirl motion creates tremendous shear forces to the exit orifice 20 thereby causing the exiting annular spray to break up into ligaments and drops. orifice 20 thereby causing the exiting annular spray to break up into ligaments and drops.

Nozzle face 22 may be flat as shown in FIG. 1. A preferred embodiment shown in FIG. 2 has nozzle face 122 in a conical shape. A parabolic nozzle face 222, as shown in FIG. 3, may also be used. The shape of the nozzle face along with the internal angle of the swirl chamber 312 may be modified to effect the desired retention, plume force, and angle of the resulting plume. FIG. 4 shows an alternate embodiment where the shape of the swirl chamber 312 has been modified to into a parabolic shape.

A corresponding nozzle back seal 24 forms the backside of the vortex chamber and is a means for manufacturing the device. Nozzle back seal 24 is inserted into back of the nozzle and extends to the very edge of the tangential passage 18 which feeds liquid into swirl chamber 12. Back seal 24 is preferably attached to the nozzle using ultrasonic welding. In essence, the back surface of the vortex nozzle is flat while the main vortex chamber is shown as primarily funnel shaped with a 90 degree cone leading to the exit orifice 20 but may be modified as aforesaid.

The above effects are achieved by careful relative dimensioning of the nozzles. The inventors have discovered that these effects are achieved when the inlet diameter 16 to outlet exit orifice diameter 18 ratio is 1:1 to 3:1, preferably 2:1; the inlet diameter 16 to swirl chamber 12 diameter ratio is 2:1 to 10:1, to preferably >5:1; the swirl chamber diameter to outlet diameter ratio is 5:1 to 20:1, preferably 10:1; the outlet diameter to outlet 18 length ratio is 0.25:1 to 4:1, preferably 1:1; and the swirl chamber cone angle B is 60 to 120 degrees, preferably 90 degrees.

The vortex nozzle is designed to produce a hollow-cone spray with a low axial velocity and impact force as it exits the nozzle orifice. Its advantages include simplicity of construction, small size, reliability and good atomization. This nozzle works well with liquids, solutions or suspensions. This nozzle is also characterized by very low plume forces and low retention within the device. The maximum absolute impact forces from the plume or spray emitted solely from this vortex nozzle are 60% of those produced by the nozzle portion of prior art devices. Additionally, because of the nature of the design of the vortex chamber, the particular nozzle described here is associated with low drug retention.

A further feature of this nozzle is that, when used with a suspension, it is self cleaning. This accounts for the very low retention of particulate at the orifice and within the swirl chamber and dose uniformity better than that of other nozzles.

The vortex nozzle may be used with (but not limited to) solutions and suspensions delivered by pressurized Metered

Figure 1:
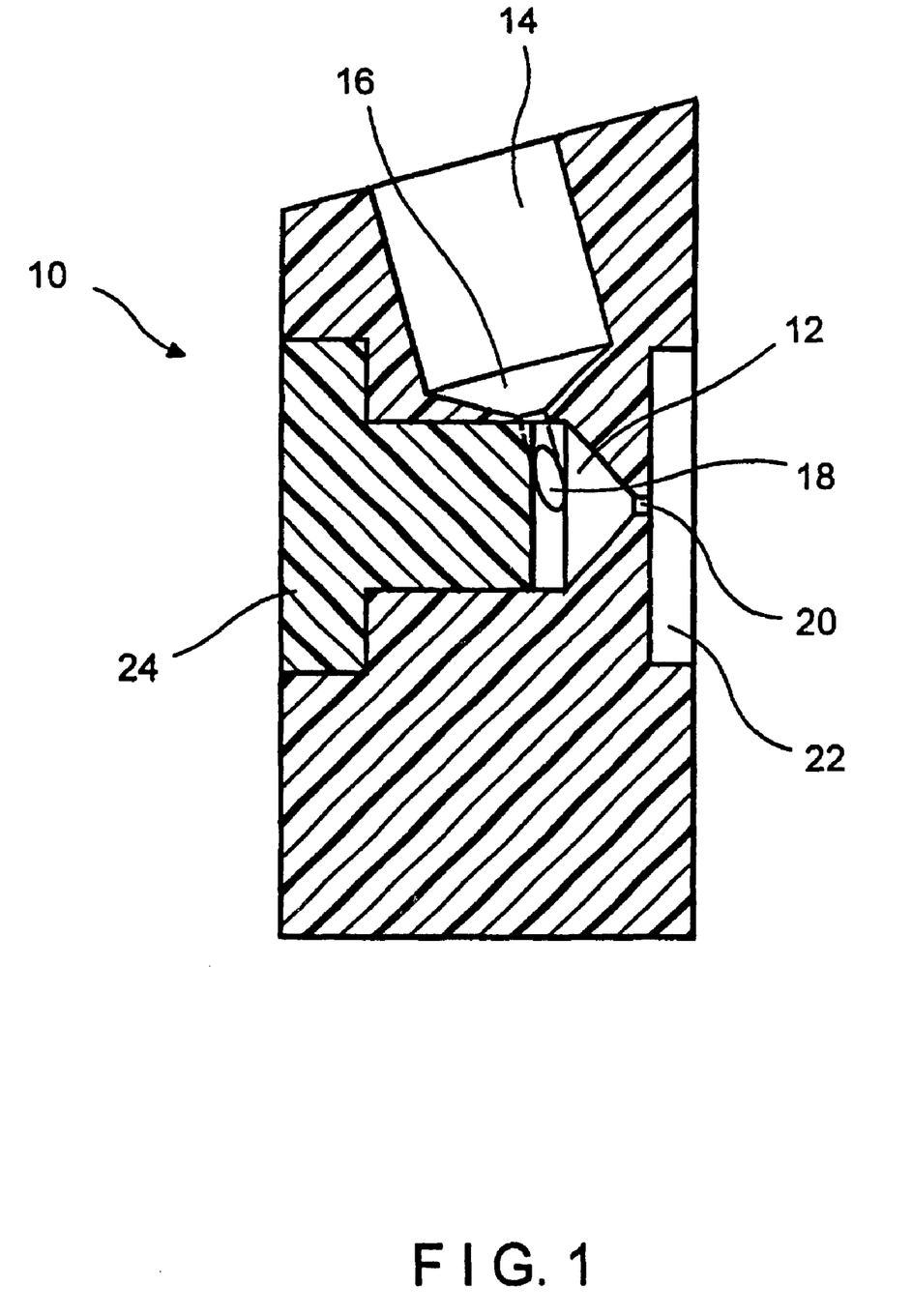
Figure 2:
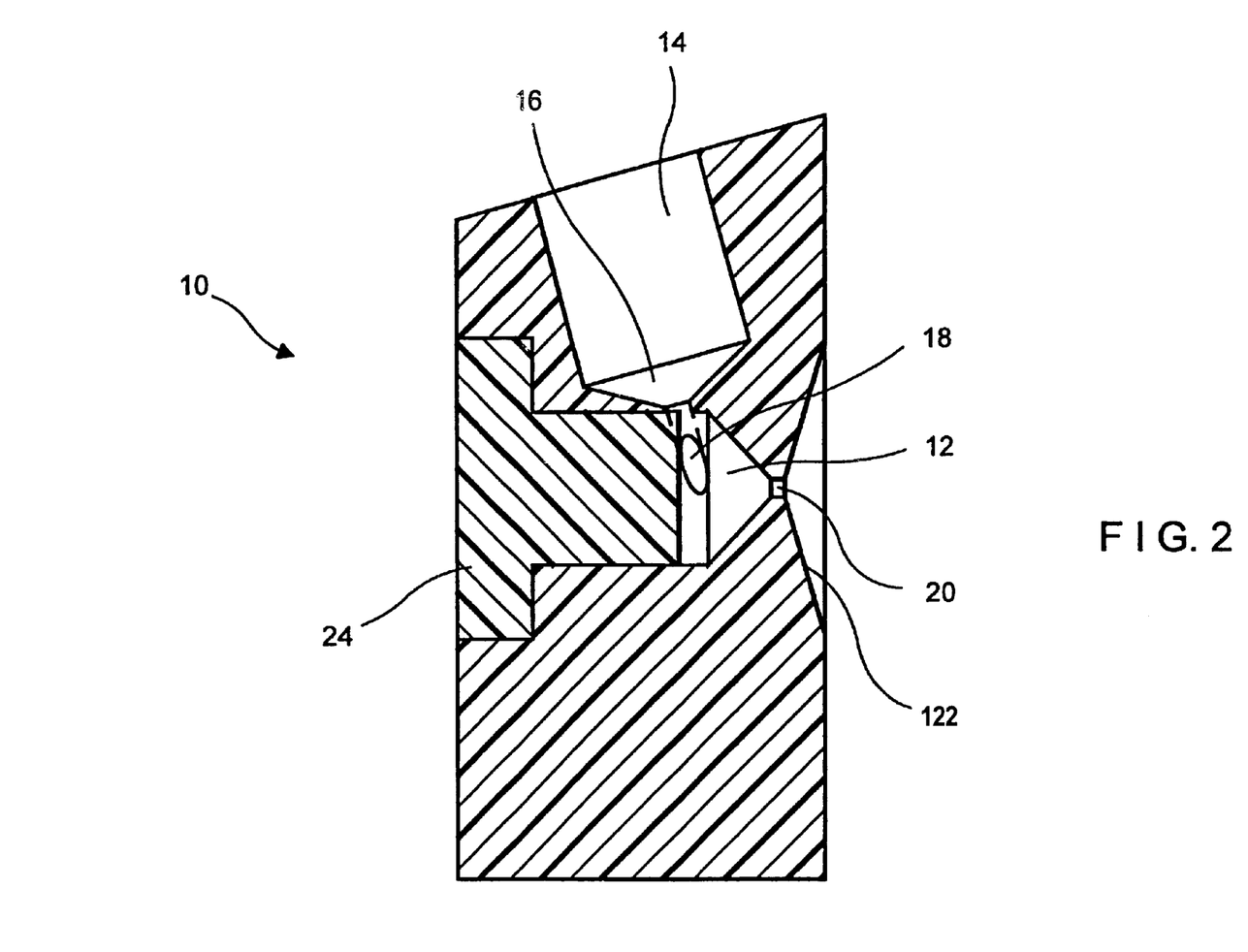
Figure 3:
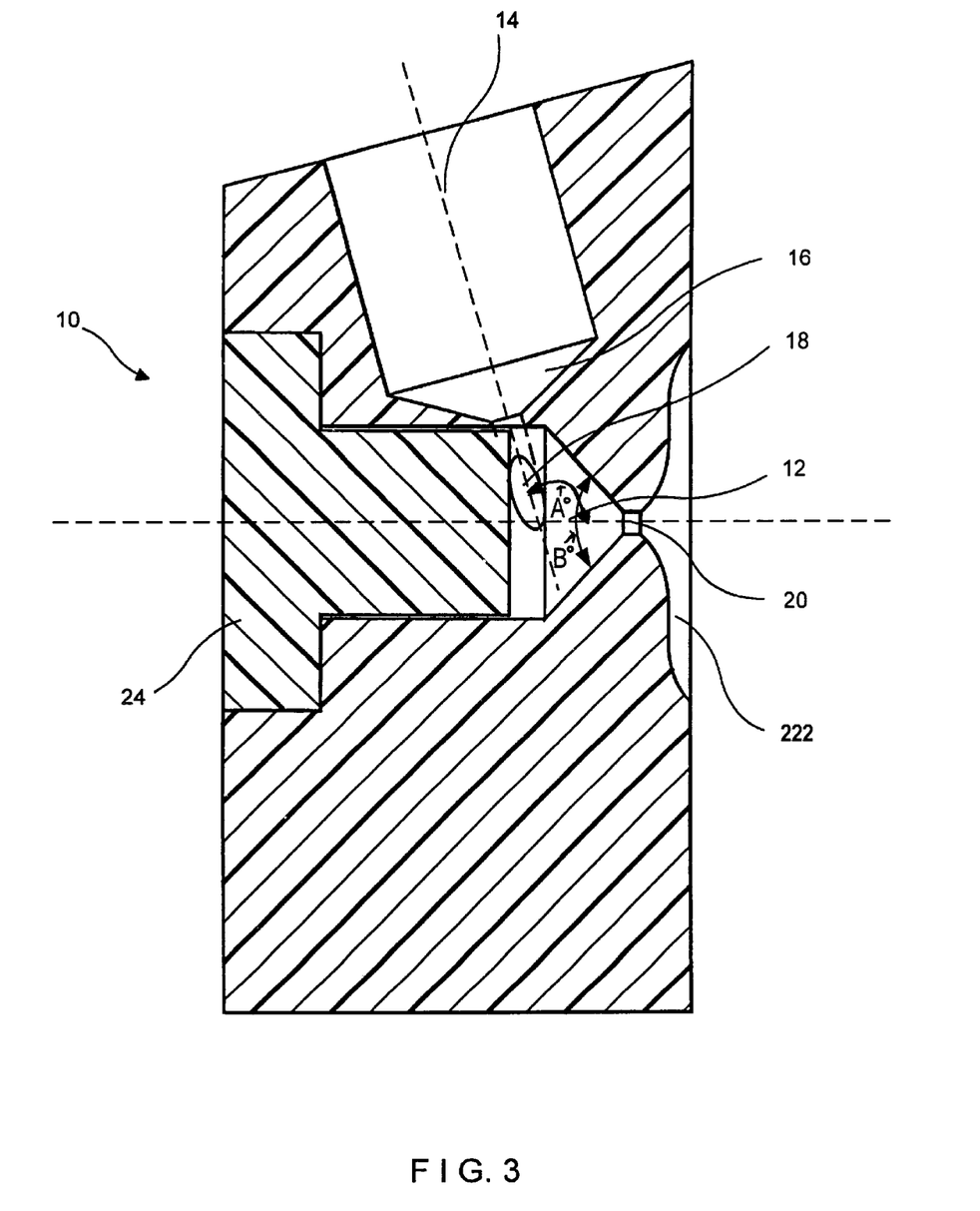
Figure 4:
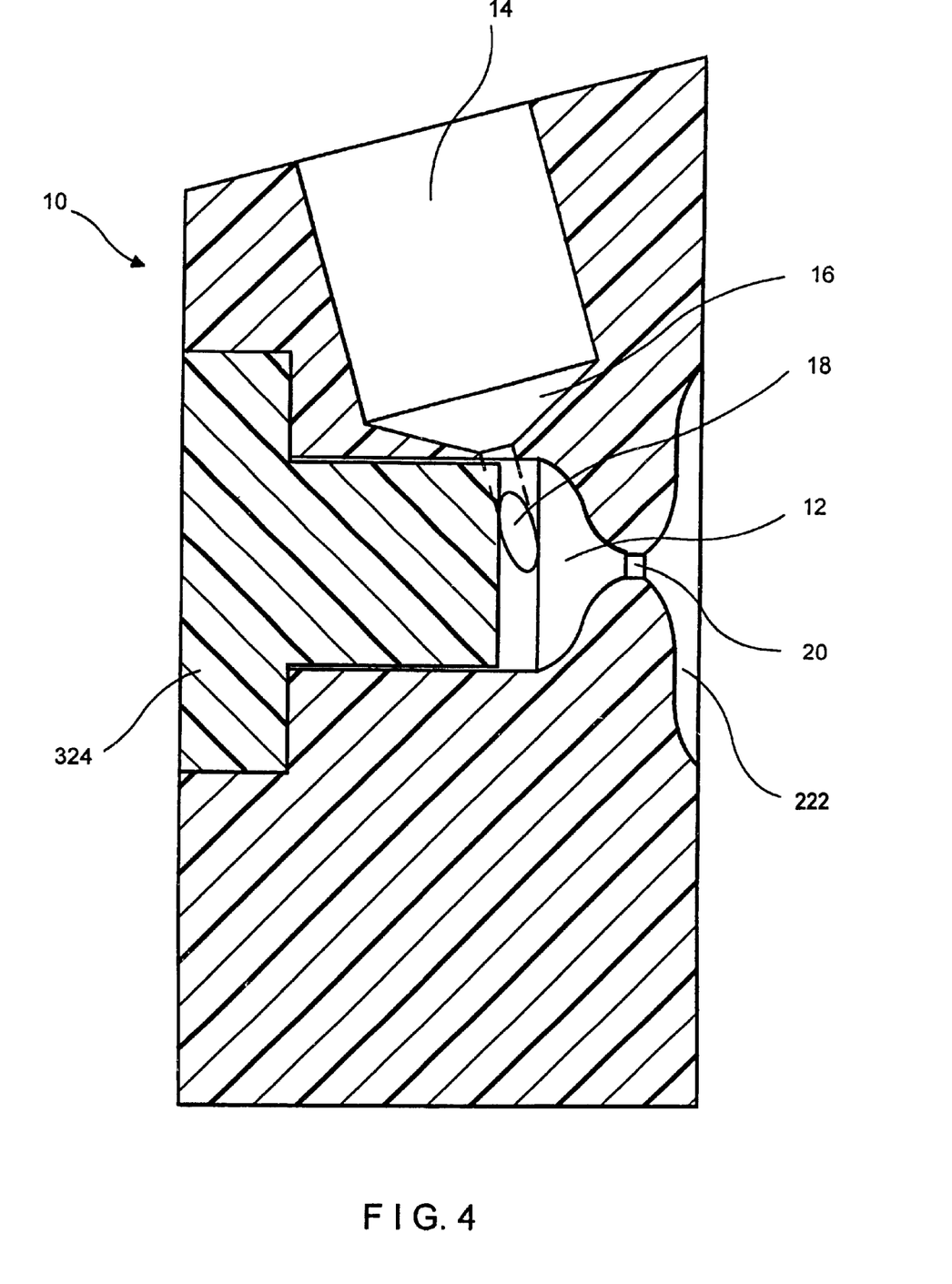
Figure 5:
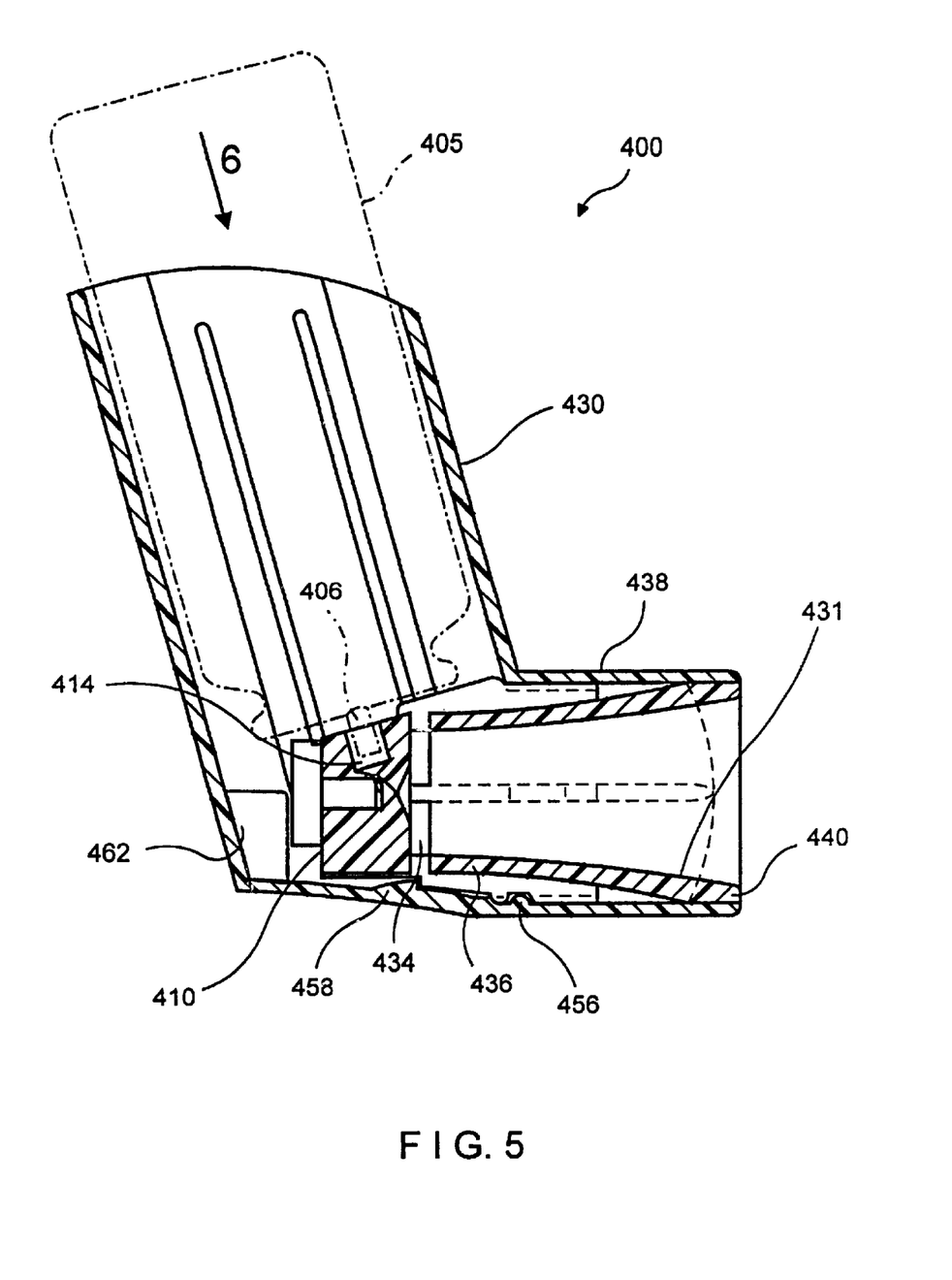
Figure 6:
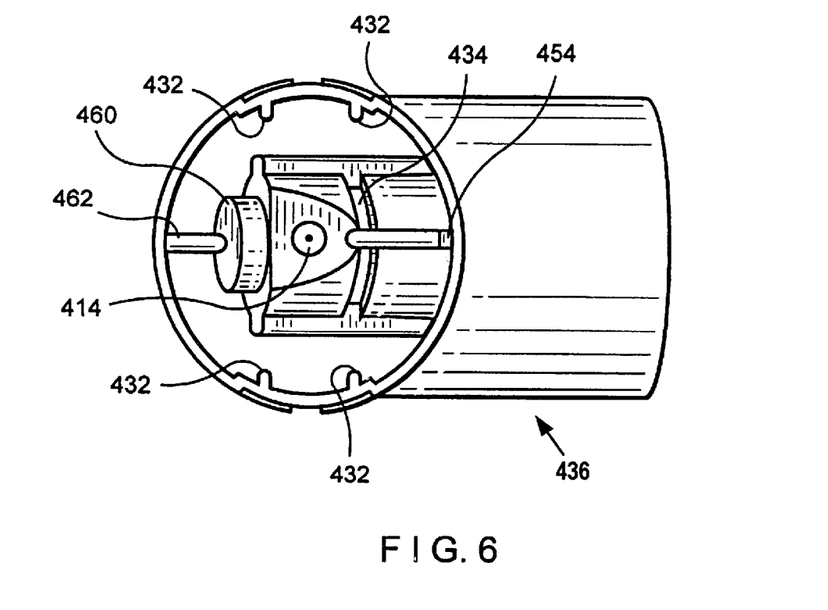
Figure 7:
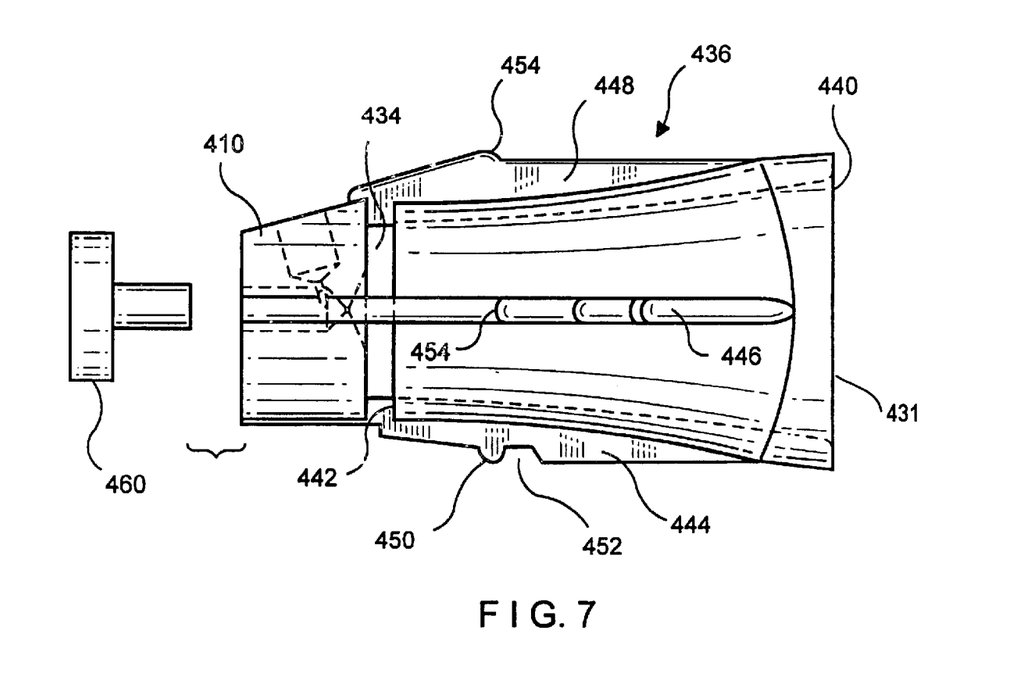

Dose Inhalers (pMDI). FIGS. 5–7 show a preferred embodiment of an integrated vortex nozzle system 400. A canister 405 shown in phantom having an outlet 406 would be disposed in inlet 414 of nozzle 410. The assembly further comprises an actuator body 430, and mouthpiece 438 with internal plume shaping geometry 431. The actuator body 430 can be of any practical shape to accept canister 405. The primary function of actuator body 430 is to align canister 405 with inlet 414 of nozzle 410. This actuator body 430 also can be designed so that a particular annular space is formed by the outside of canister 405 and the inside of actuator body 430. In this regard longitudinal ribs 432 are provided to provide air passage channels between canister 405 and body 430. This space is used to control the amount of air flowing past canister 405 and ultimately past nozzle 410 and through radial slits 434 in mouthpiece insert 436 and subsequently through the mouthpiece insert's internal geometry 431.

Turning now briefly to FIG. 7, there is shown mouthpiece insert 436 which is intended to be inserted into the mouthpiece portion 438 of actuator body 430. Insert 436 has a forward or open end 440 and a rearward end 442. Coupled at end 442 is nozzle 410 by way of ribs 444, 446 and 448. Rib 446 has an opposite rib (not shown). Nozzle 410 is positioned at a spaced distance from end 442 so as to create slits 434. Rib 444 or the bottom rib includes a raised nub 450 and adjacent slot 452. The other ribs include nubs 454. As can be seen in FIG. 5, when the mouthpiece insert 436 is inserted into mouthpiece portion 438, nubs 454 engage the upper inner circumference of annular body 430 as shown with nub 450 passing over nub 456 which snaps into position in slot 452. A raised stop 458 is provided in body 430 which engages the rear of rib 444, all of which serves to lock insert 436 in place.

As shown in FIG. 7, a back seal or plug 460 is provided for insertion into the rear of nozzle 410. In this regard, nozzle 410 and insert 436 may be fabricated integrally or separately and then coupled together in an appropriate means suitable for purpose. The material used may be HDPE or any other appropriate material. Plug 460 may be made of a somewhat resilient material as to allow for its insertion into the back of nozzle 410. As can be seen in FIGS. 5 and 6, upon completion of insertion of insert 436, plug 460 abuts flange 462 on body 430. This assures plug 460 stops in place and also helps maintain the proper position of inlet 414. be seen in FIGS. 5 and 6, upon completion of insertion of insert 436, plug 460 abuts flange 462 on body 430. This assures plug 460 stops in place and also helps maintain the proper position of inlet 414.

Turning briefly to FIG. 6, this is a view down body 430 prior to insertion of a canister. In this regard, insert 436 has been fully inserted and snapped in place. Inlet 414 is now properly aligned to receive canister outlet 406. Ribs 432 will ensure the proper insertion of canister 405 into body 430. The ribs will also provide for passageways for air around the canister 405. In this regard, when the user inhales upon the mouthpiece portion 438 whilst depressing the canister 405, the medication is dispensed via the vortex nozzle as previously discussed into the mouthpiece. The inhalation by the user draws air down around the canister 405 and through slits 434 into the mouthpiece which along with the medication is inhaled by the patient.

It should be noted that the degree of opening of the slits may be adjusted to control the amount of air mixed with the spray emitted from nozzle 410 within internal geometry 431. Internal geometry 431 serves to diffuse and shape the plume while further reducing the force of the emitted spray. This internal geometry 431 may assume a variety of shapes and features depending on the desired qualities of the exiting plume. The spray entering internal geometry 431 with entrained air is presented at the mouthpiece outlet. The internal geometry 431 of mouthpiece 434 is designed to decelerate the outermost layer of the spray. This deceleration of the boundary layer is a critical in reducing the overall force of the spray exiting the mouthpiece. The specific design of the internal geometry 431 and the air gap between the nozzle exit and the mouthpiece inlet can be tailored to the exact configuration of the nozzle to provide desired results.

Note that rather than slits or perhaps in addition thereto, perforations could be positioned all about insert 436 to allow air to enter the internal geometry thereof. The number and size of the holes can be adjusted to provide the desired amount of inhalation make-up air and pressure drop through the device. The application of these holes may be tailored to minimize retention along the internal geometry 431.

Thus the inventive nozzle provides several advantages including: a simple low cost construction; utility with liquids, solutions and suspensions; a low output plume force; a low operating pressure; a low solids retention when used with suspensions; adjustable particle size; adjustable plume force; smooth internal surfaces to reduce frictional losses; compatible shot duration with traditional pMDI actuation; adjustable shot duration; and a direct replacement for traditional pump based pMDI nozzles. Those skilled in the art will appreciate alternate applications for the inventive nozzle envisioned including, particularly (but not limited to), use with other suspensions such as paints and plasticizers, and microparticles such as fine powders.

What is claimed is:

1. A nozzle for producing low-plume aerosolized sprays comprised of:
    a nozzle housing including an inlet which opens into a swirl chamber having an outer circumference, a diameter and a first swirl chamber end having a diameter, the inlet being tangential to the outer circumference and set at an angle to the first swirl chamber end, an exit passage positioned at a second swirl chamber end having a diameter, the diameter of the first swirl chamber end having a diameter greater than the diameter of the second swirl chamber end, the exit passage communicating with a nozzle face through which an aerosol is discharged.

2. The nozzle as set forth in claim 1 wherein the diameter of the swirl chamber decreases along a path between the first swirl chamber end and the second swirl chamber end.

3. The nozzle as set forth in claim 1 wherein the exit passage has a diameter which is substantially the same as the diameter of the second swirl chamber end.

4. The nozzle as set forth in claim 1 wherein the nozzle face has a diameter which is substantially greater than the diameter of the exit passage.

5. The nozzle as set forth in claim 1 wherein the nozzle face is flat.

6. The nozzle as set forth in claim 1 wherein the nozzle face is conical.

7. The nozzle as set forth in claim 1 wherein the swirl chamber has a conical shape.

8. The nozzle as set forth in claim 7 wherein the swirl chamber has a cone angle is 60 to 120 degrees.

9. The nozzle as set forth in claim 1 wherein the swirl chamber has a parabolic shape.

10. The nozzle as set forth in claim 1 wherein the inlet is set at angle of 105 degrees to an axis of the swirl chamber.

11. The nozzle as set forth in claim 1 wherein the inlet is set at an angle of 90 degrees to an axis of the swirl chamber.

12. An inhaler for generating a low-plume aerosolized spray comprising:

a housing for receiving a canister of pressurized medication;

said housing including a mouthpiece for dispensing medication therefrom to a user;

a nozzle housing including an inlet which opens into a swirl chamber having an outer circumference, a diameter and a first swirl chamber end having a diameter, the inlet being tangential to the outer circumference and set at an angle to the first swirl chamber end, an exit passage positioned at a second swirl chamber end having a diameter, the diameter of the first swirl chamber end having a diameter greater than the diameter of the second swirl chamber end, the exit passage communicating with a nozzle face through which an aerosol is discharged;

said inlet being adapted to be in fluid communication with the canister;

said nozzle face being positioned to discharge an aerosolized spray into the mouthpiece; and passageway means for allowing air to pass into and out of the mouthpiece.

13. An inhaler in accordance with claim 12 which further comprises:

mouthpiece insert having a front and rear end coupled to the nozzle at the rear end;

said front end being located so as to discharge the spray out of the mouthpiece; and said passageway means comprising at least one opening in the insert so as to allow air to pass therethrough and out the mouthpiece.

14. The inhaler in accordance with claim 13 wherein the diameter of the swirl chamber decreases along a path between the first swirl chamber end and the second swirl chamber end.

15. The inhaler in accordance with claim 13 wherein the exit passage has a diameter which is substantially the same as the diameter of the second swirl chamber end.

16. The inhaler in accordance with claim 13 wherein the nozzle face has a diameter which is substantially greater than the diameter of the exit passage.

17. The inhaler in accordance with claim 13 wherein the nozzle face is flat.

18. The inhaler in accordance with claim 13 wherein the nozzle face is conical.

19. The inhaler in accordance with claim 13 wherein the swirl chamber has a conical shape.

20. The inhaler in accordance with claim 13 wherein the swirl chamber has a parabolic shape.

21. The inhaler in accordance with claim 13 wherein the inlet is set at an angle of 105 degrees to an axis of the swirl chamber.

22. The inhaler in accordance with claim 13 wherein the inlet is set at an angle of 90 degrees to an axis of the swirl chamber.

23. The inhaler in accordance with claim 13 wherein the swirl chamber has a cone angle is 60 to 120 degrees.

\* \* \* \* \*